US00PP31317P2

(12) United States Plant Patent
Hooper

(10) Patent No.: US PP31,317 P2
(45) Date of Patent: Jan. 7, 2020

(54) ***MAGNOLIA* PLANT NAMED 'TINKERBELLE'**

(50) Latin Name: *Magnolia soulangeana*
Varietal Denomination: Tinkerbelle

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 0 days.

(21) Appl. No.: 16/350,666

(22) Filed: Dec. 18, 2018

(51) Int. Cl.
*A01H 5/00* (2018.01)
*A01H 6/00* (2018.01)

(52) U.S. Cl.
USPC ..... Plt./223

(58) Field of Classification Search
USPC ..... Plt./216, 223
See application file for complete search history.

*Primary Examiner* — Susan McCormick Ewoldt
*Assistant Examiner* — Karen M Redden

(57) ABSTRACT

A new cultivar of *Magnolia* plant named 'Tinkerbelle' that is characterized by upright cup shaped flowers having red-purple tepals, slender upright oriented branches, terminal flowers that are normally solitary and flowers that maintain their color during the flowering season.

2 Drawing Sheets

Botanical classification: *Magnolia soulangeana.*
Variety denomination: 'Tinkerbelle'.

BACKGROUND OF THE INVENTION

The present invention relates to a new and distinct cultivar of *Magnolia* plant botanically known as *Magnolia soulangeana* and hereinafter referred to by the cultivar name 'Tinkerbelle'.

The new cultivar is the product of a breeding program conducted by the inventor in a cultivated area of Waitara, New Zealand. The objective of the breeding program is to develop new *Magnolia* cultivars that have attractive flower colors.

'Tinkerbelle' originated from crossing the female or seed parent *Magnolia soulangeana* 'Sweet Simplicity' (not patented) and the male or pollen parent *Magnolia soulangeana* 'Cameo' (U.S. Plant Pat. No. 27,222). The crossing was conducted in 2002 in a controlled environment. The cultivar 'Tinkerbelle' was selected by the inventor in 2009 as a single plant within the progeny of the stated cross in a cultivated area of Waitara, New Zealand.

Asexual reproduction of the new cultivar 'Tinkerbelle' by budding was first performed in 2009 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Magnolia* cultivar 'Tinkerbelle'. These traits in combination distinguish 'Tinkerbelle' as a new and distinct cultivar.

1. *Magnolia* 'Tinkerbelle' exhibits upright cup shaped flowers having red-purple tepals.
2. *Magnolia* 'Tinkerbelle' exhibits slender upright oriented branches.

3. *Magnolia* 'Tinkerbelle' exhibits terminal flowers that are normally solitary.
4. *Magnolia* 'Tinkerbelle' exhibits flowers that maintain their color during the flowering season.

The closest comparison varieties are *Magnolia* 'Genie' (U.S. Plant Pat. No. 20,748) and the male parent plant *Magnolia* 'Cameo'. 'Tinkerbelle' is different than 'Genie' in the following characteristics:

1. *Magnolia* 'Tinkerbelle' exhibits upright cup shaped flowers having red-purple tepals. In contrast, the flowers of 'Genie' are less cup shaped and more spreading.
2. *Magnolia* 'Tinkerbelle' exhibits slender upright oriented branches. In contrast, the branches of 'Genie' are less upright and are oriented at larger angles from vertical.
3. *Magnolia* 'Tinkerbelle' exhibits terminal flowers that are normally solitary. In contrast, 'Genie' exhibits terminal flowering with secondary and tertiary flowers.

'Tinkerbelle' is different than 'Cameo' in the following characteristics:

1. *Magnolia* 'Tinkerbelle' exhibits upright cup shaped flowers having red-purple tepals.

In contrast, the flowers of 'Cameo' are less cup shaped and more spreading.

2. *Magnolia* 'Tinkerbelle' exhibits slender upright oriented branches. In contrast, the branches of 'Cameo' are thicker and are oriented at larger angles from vertical.
3. *Magnolia* 'Tinkerbelle' exhibits terminal flowers that are normally solitary. In contrast, 'Cameo' exhibits terminal flowering with secondary flowers.

'Tinkerbelle' is different than the female parent plant 'Sweet Simplicity' in the following characteristics:

1. *Magnolia* 'Tinkerbelle' exhibits upright cup shaped flowers having red-purple tepals. In contrast, the flowers of 'Sweet Simplicity' are less cup shaped and more spreading.
2. *Magnolia* 'Tinkerbelle' exhibits slender upright oriented branches. In contrast, the branches of 'Sweet Simplicity' are thicker and are oriented at larger angles from vertical.

3. *Magnolia* 'Tinkerbelle' exhibits terminal flowers that are normally solitary. In contrast, 'Sweet Simplicity' exhibits terminal flowering with secondary flowers.

BRIEF DESCRIPTION OF THE DRAWING

The accompanying photographs illustrate the distinguishing traits of *Magnolia* 'Tinkerbelle'.

The photograph on sheet 1 shows an overall view of a 4 year old plant.

The photograph on sheet 2 shows a view of the foliage.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Magnolia* cultivar named 'Tinkerbelle'. Data was collected in Waitara, New Zealand from 4 year old field grown plants. The time of year was Spring and the average temperature was 14° Centigrade during the day and 8° Centigrade at night. Color determinations are in accordance with The Royal Horticultural Society Colour Chart 2001 edition, except where general color terms of ordinary dictionary significance are used. The growing requirements are similar to the species. 'Tinkerbelle' has not been tested under all possible conditions and phenotypic differences may be observed with variations in environmental, climatic, and cultural conditions, however, without any variance in genotype.

Botanical classification: *Magnolia soulangeana* 'Tinkerbelle'.

Use: Ornamental tree.

Parentage: 'Tinkerbelle' is a hybrid of the female or seed parent *Magnolia soulangeana* 'Sweet Simplicity' and the male or pollen parent *Magnolia soulangeana* 'Cameo'.

Container size: 10 liter.

Vigor: Moderately strong

Growth rate: 40 to 50 cm. per year on upright shoots, 20 to 30 cm. per year on lateral branches.

Growth habit: Upright.

Plant shape: Upright columnar.

Height: Average 1.5 m. in height.

Width: Average 80 cm. in width.

Hardiness: −15° to 35° C.

Propagation: Field budding, tissue culture and cuttings.

Crop time: 1 year from grafting.

Stem:

- *Branching habit.*—Primary branching upward with shorter secondary branching.
- *Number of lateral branches.*—5 to 7.
- *Lateral branch diameter.*—5 to 7 mm. in diameter.
- *Lateral branch length.*—20 to 30 cm. in length.
- *Internode length.*—35 to 40 mm. between nodes.
- *Stem color.*—Immature stems 144A, mature stems N200C.
- *Stem aspect.*—Vertical main stem, lateral braches oriented upward.
- *Pubescence.*—Absent.
- *Shape.*—Round.
- *Surface.*—Smooth.
- *Lateral branch strength.*—Moderately strong.
- *Lenticels.*—1 to 2 mm. in length, color 156C, density 1 per square cm.
- *Pinching: Usually at* 1.2 meters in height, if not flowered.

Foliage:

- *Leaf arrangement.*—Alternate.
- *Compound or single.*—Single.
- *Quantity of leaves per lateral branch:* 5 to 8.
- *Leaf shape.*—Elliptic to obovate.
- *Leaf apex.*—Acute.
- *Leaf base.*—Cuneate.
- *Leaf length.*—12.5 to 18.0 cm. in length.
- *Leaf width.*—6.0 to 9.5 cm. in width.
- *Pubescence.*—Absent on both surfaces.
- *Texture.*—Both surfaces slightly leathery.
- *Leaf margin.*—Entire.
- *Vein pattern.*—Pinnate.
- *Young leaf color* (*upper surface*).—146C.
- *Young leaf color* (*lower surface*).—144A.
- *Mature leaf color* (*upper surface*).—137A.
- *Mature leaf color* (*lower surface*).—137C.
- *Vein color* (*upper surface*).—146C.
- *Vein color* (*lower surface*).—194A.
- *Leaf attachment.*—Petiolate.
- *Petiole dimensions.*—10 to 15 mm. in length, 3 to 5 mm. in width.
- *Petiole color.*—Upper side 152B, lower side 137C.
- *Durability of foliage to stress.*—High, resistant to wind damage and sunburn.

Flower:

- *Flower arrangement.*—Solitary terminal cup shaped flowers held upright.
- *Quantity of flowers per lateral stem.*—1.
- *Quantity of flower buds per lateral stem.*—1.
- *Quantity of flowers and buds per plant.*—Approximately 25.
- *Flowering habit.*—Flowers bloom in Spring before foliage appears.
- *Flowering season.*—Spring to Summer.
- *Time to flower or response time.*—5 to 7 weeks after breaking dormancy.
- *Fragrance.*—Sweet citrus scent.
- *Self-cleaning or persistent.*—Self cleaning.
- *Flower bud length.*—20 mm. in length.
- *Flower bud diameter.*—10 mm. in diameter.
- *Flower bud shape.*—Slender ovate.
- *Rate of bud opening.*—10 to 14 days.
- *Bud color.*—N77A.
- *Flower aspect.*—Upright.
- *Flower shape.*—Cup shaped.
- *Flower dimensions.*—7 to 10 cm. in diameter and 7.5 to 8.5 cm. in height.
- *Flower longevity.*—Lasts approximately 7 to 10 days on plant.
- *Flower longevity as a cut flower.*—Lasts approximately 7 days.
- *Tepal arrangement.*—Whorled.
- *Number of tepals.*—6 to 8 in number.
- *Fused or unfused.*—Not fused.
- *Tepal shape.*—Ovate.
- *Tepal margin.*—Entire.
- *Tepal apex.*—Rounded.
- *Tepal base.*—Rounded.
- *Tepal texture.*—Smooth both surfaces.
- *Tepal appearance.*—Matte both surfaces.
- *Tepal dimensions.*—6.6 to 7.6 cm. in length and 4.0 to 5.0 cm. in width.

*Tepal color when opening* (*upper side*): 79C.
*Tepal color when opening* (*under side*): 187A.
*Tepal color when fully opened* (*upper side*): 71B.
*Tepal color when fully opened* (*under side*): 187A suffused with 72B.
*Tepal color fading to.*—72B.

Sepals:
*Number of sepals.*—4 or 5.
*Sepal dimensions.*—13 mm. in length and 6 mm. in width.
*Sepal shape.*—Ovate.
*Sepal tip.*—Acute.
*Sepal base.*—Cuneate.
*Sepal margin.*—Entire.
*Sepal color.*—Upper side 77B, lower side N77C with stripes N77B.

Peduncle:
*Peduncle dimensions.*—2 mm. in length and 8 mm. in diameter.
*Peduncle angle.*—Vertical.
*Peduncle strength.*—Strong.
*Peduncle color.*—145C.

Reproduction organs:
*Stamen number.*—60 to 80.
*Anther shape.*—Curved.
*Anther Length.*—7 mm. in length.
*Anther color.*—Base 187A, tip N79C.
*Amount of pollen.*—Moderate.
*Pollen color.*—2D.
*Pistil number.*—1 in number.
*Pistil length.*—14 mm.
*Stigma shape.*—Curved.
*Stigma color.*—187B.
*Style length.*—0.9 mm.
*Style color.*—187A.
*Ovary color.*—187A. Fruit and seed production has not been observed to date.

Disease and pest resistance: Exhibits good resistance to mildew.

The invention claimed is:

1. A new and distinct variety of *Magnolia* plant named 'Tinkerbelle' as described and illustrated.

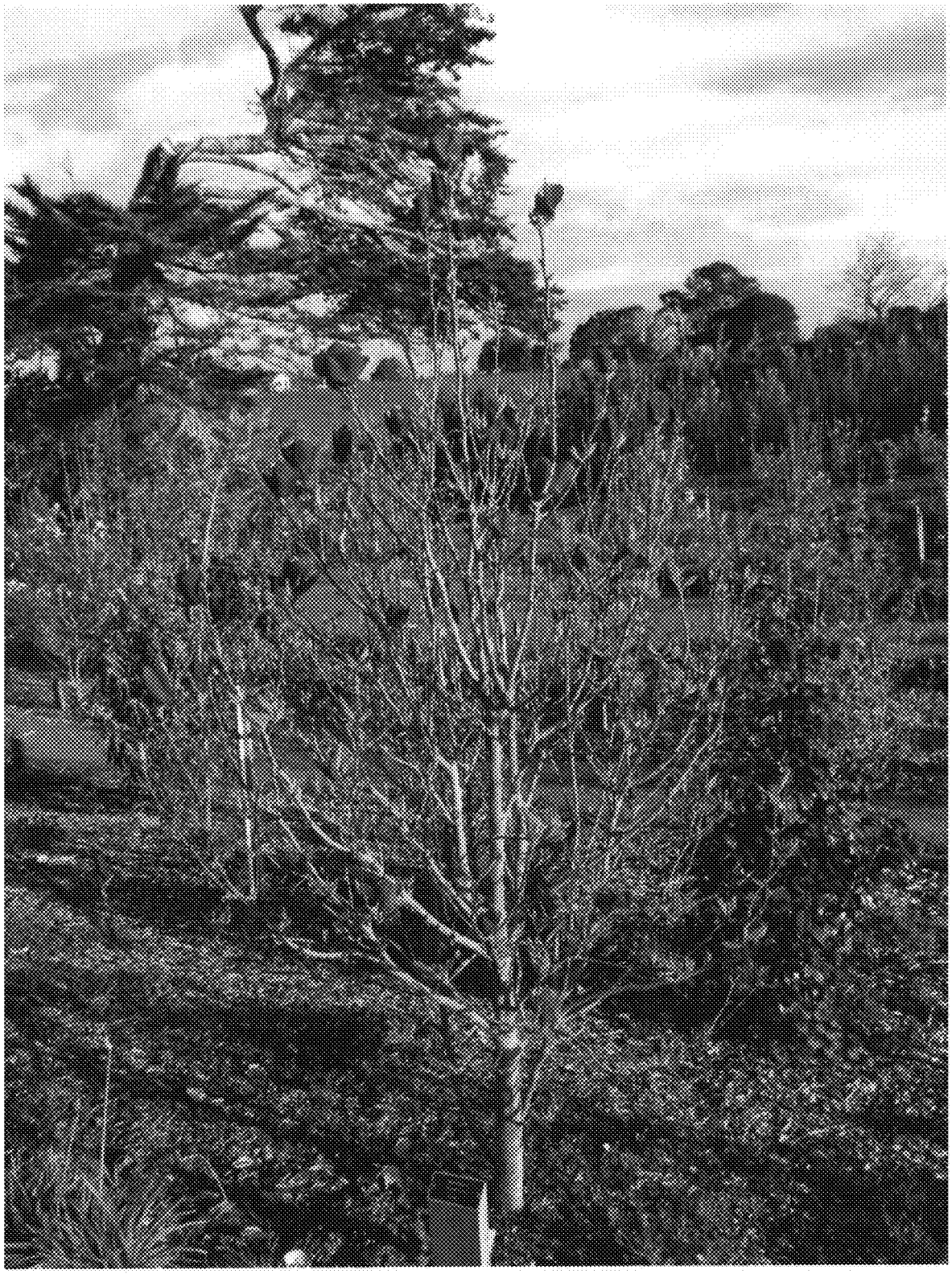

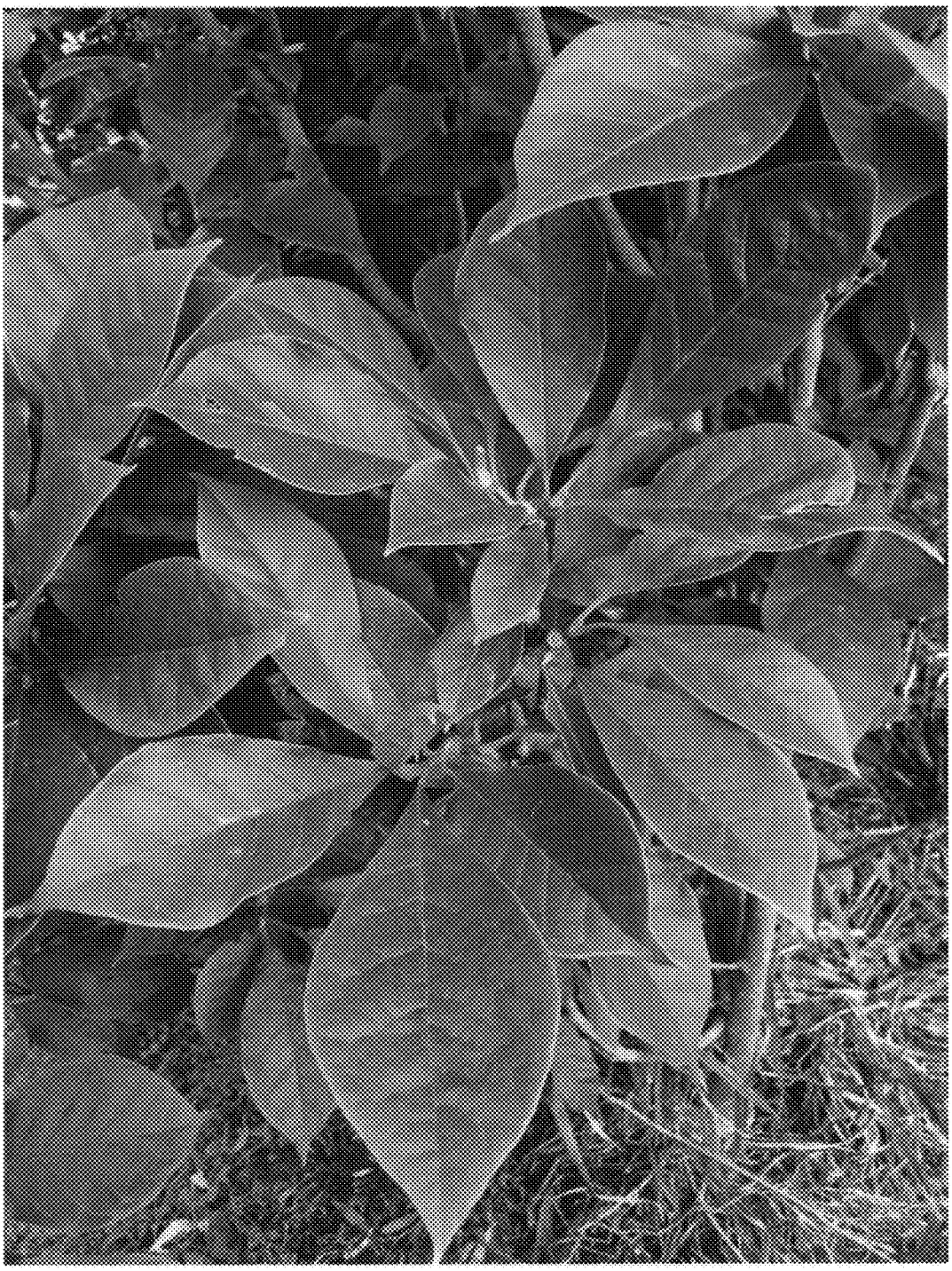

* * * * *